US011021498B2

(12) United States Patent
Muhammad et al.

(10) Patent No.: US 11,021,498 B2
(45) Date of Patent: *Jun. 1, 2021

(54) WATER-SOLUBLE ACETAMINOPHEN ANALOGS

(71) Applicant: Acorda Therapeutics, Inc., Ardsley, NY (US)

(72) Inventors: Naweed Muhammad, Fremont, CA (US); Keith R. Bley, Menlo Park, CA (US)

(73) Assignee: Acorda Therapeutics, Inc., Ardsley, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/565,173

(22) Filed: Sep. 9, 2019

(65) Prior Publication Data
US 2020/0002364 A1    Jan. 2, 2020

Related U.S. Application Data

(63) Continuation of application No. 15/962,934, filed on Apr. 25, 2018, now Pat. No. 10,442,826, which is a continuation of application No. 15/077,802, filed on Mar. 22, 2016, now Pat. No. 9,981,998, which is a continuation of application No. 12/993,088, filed as application No. PCT/US2009/044743 on May 20, 2009, now abandoned.

(60) Provisional application No. 61/054,774, filed on May 20, 2008.

(51) Int. Cl.
*A61K 9/00* (2006.01)
*A61K 45/06* (2006.01)
*A61K 31/661* (2006.01)
*C07F 9/09* (2006.01)
*A61P 29/02* (2006.01)
*A61P 29/00* (2006.01)
*A61P 9/00* (2006.01)
*A61P 9/10* (2006.01)
*A61P 25/04* (2006.01)
*A61P 25/00* (2006.01)
*A61P 43/00* (2006.01)

(52) U.S. Cl.
CPC ............ *C07F 9/094* (2013.01); *A61K 9/0019* (2013.01); *A61K 31/661* (2013.01); *A61K 45/06* (2013.01); *C07F 9/091* (2013.01)

(58) Field of Classification Search
CPC ........ A61K 9/0019; A61K 9/00; A61K 45/06; A61K 31/661; C07F 9/091; C07F 9/094; C07F 9/09; A61P 29/02; A61P 29/00; A61P 9/00; A61P 9/10; A61P 25/04; A61P 25/00; A61P 43/00
See application file for complete search history.

(56) References Cited

U.S. PATENT DOCUMENTS

| 4,322,410 | A | 3/1982 | Stjepanovic et al. |
| 5,001,115 | A | 3/1991 | Sloan |
| 5,073,641 | A | 12/1991 | Bundgaard et al. |
| 5,272,171 | A | 12/1993 | Ueda et al. |
| 5,498,729 | A | 3/1996 | Domb |
| 5,939,405 | A | 8/1999 | Starrett, Jr. et al. |
| 5,985,856 | A | 11/1999 | Stella et al. |
| 6,043,285 | A | 3/2000 | Pinza et al. |
| 6,140,310 | A | 10/2000 | Glazier |
| 6,204,257 | B1 * | 3/2001 | Stella .................... C07K 7/645 514/130 |
| 6,214,811 | B1 | 4/2001 | Glazier et al. |
| 6,362,172 | B2 | 3/2002 | Ueda et al. |
| 6,451,776 | B2 | 9/2002 | Stella et al. |
| 6,713,089 | B1 | 3/2004 | Bertelsen et al. |
| 6,825,204 | B2 | 11/2004 | Liu |
| 6,872,838 | B2 | 3/2005 | Stella et al. |
| 6,916,825 | B2 | 7/2005 | Senn-Bilfinger et al. |
| 7,230,005 | B2 | 6/2007 | Shafer et al. |
| 7,244,718 | B2 | 7/2007 | Stella et al. |
| 8,735,376 | B2 | 5/2014 | Muhammad et al. |
| 8,993,545 | B2 | 3/2015 | Muhammad et al. |
| 9,024,055 | B2 | 5/2015 | Bley et al. |
| 9,289,501 | B2 | 3/2016 | Muhammad et al. |
| 9,683,000 | B2 | 6/2017 | Muhammad et al. |
| 9,981,998 | B2 | 5/2018 | Muhammad et al. |

(Continued)

FOREIGN PATENT DOCUMENTS

| WO | WO-00/08033 A1 | 2/2000 |
| WO | WO-01/52852 A1 | 7/2001 |

(Continued)

OTHER PUBLICATIONS

Baliga, S.S. (May 2009). "Acetaminophen Confers Neuroprotection During Early Cerebral Ischemia-Reperfusion," A Dissertation submitted to the Graduate School—New Brunswick Rutgers, The State University of New Jersey and the Graduate School of Biomedical Sciences University of Medicine and Dentistry and Dentistry of New Jersey, 125 pages.

(Continued)

*Primary Examiner* — Sun Jae Yoo

(74) *Attorney, Agent, or Firm* — Morrison & Foerster LLP

(57) ABSTRACT

The present invention provides water-soluble acetaminophen prodrugs and formulations which may be suitable for parenteral administration. Methods of treating a disease or condition responsive to acetaminophen (such as fever and/or pain) using the acetaminophen prodrugs, as well as kits, unit dosages, and combinations with additional pharmaceutical agent(s) are also provided.

1 Claim, 3 Drawing Sheets

(56) References Cited

U.S. PATENT DOCUMENTS

| | | |
|---|---|---|
| 2002/0090398 A1 | 7/2002 | Dunn et al. |
| 2003/0022876 A1 | 1/2003 | Ashton et al. |
| 2004/0058946 A1 | 3/2004 | Buchwald et al. |
| 2004/0186081 A1 | 9/2004 | Slusher et al. |
| 2005/0020576 A1 | 1/2005 | Zhang et al. |
| 2005/0026850 A1 | 2/2005 | Robinson et al. |
| 2005/0026879 A1 | 2/2005 | Robinson et al. |
| 2005/0080260 A1 | 4/2005 | Mills et al. |
| 2005/0147668 A1 | 7/2005 | Bertelsen et al. |
| 2006/0089383 A1 | 4/2006 | Le Bourdonnec et al. |
| 2006/0116422 A1 | 6/2006 | De Groot et al. |
| 2007/0042999 A1 | 2/2007 | West et al. |
| 2008/0318905 A1 | 12/2008 | Muhammad et al. |
| 2010/0234452 A1 | 9/2010 | Mian et al. |
| 2011/0212926 A1 | 9/2011 | Muhammad et al. |
| 2011/0263545 A1 | 10/2011 | Muhammad et al. |
| 2014/0243407 A1 | 8/2014 | Bley et al. |
| 2016/0326107 A1 | 11/2016 | Muhammad et al. |
| 2018/0086778 A1 | 3/2018 | Muhammad et al. |
| 2019/0092795 A1 | 3/2019 | Muhammad et al. |

FOREIGN PATENT DOCUMENTS

| | | |
|---|---|---|
| WO | WO-2005/077394 A1 | 8/2005 |
| WO | WO-2006/014282 A2 | 2/2006 |
| WO | WO-2006/014282 A3 | 2/2006 |
| WO | WO-2009/143295 A1 | 11/2009 |
| WO | WO-2009/143297 A1 | 11/2009 |
| WO | WO-2009/143299 A1 | 11/2009 |
| WO | WO-2010/030781 A2 | 3/2010 |
| WO | WO-2010/030781 A3 | 3/2010 |
| WO | WO-2013/044064 A1 | 3/2013 |

OTHER PUBLICATIONS

Berenblum, I. et al. (1959). "Skin-Initiating Action and Lung Carcinogenesis by Derivatives of Urethane (Ethyl Carbamate) and Related Compounds," Biochemical Pharmacology 2:168-176.

clinicaltrials.gov. (Dec. 2015). NCT01120769. "Acetaminophen to Prevent Ischemic Oxidative Reperfusion Injury During Percutaneous Coronary Intervention for Acute Myocardial Infarction," located at < https://clinicaltrials.gov/ct2/show/NCT01120769>, last visited on Jul. 11, 2017, 4 pages.

De Jong, R.S. et al. "Randomized comparison of etoposide pharmacokinetics after oral etoposide phosphate and oral etoposide" British Journal of Cancer (1997) 75(11), 1660-1666.

drugs.com. (2017). "Is Tylenol an Anti-Inflammatory Drug?," located at < https://www.drugs.com/answers/tylenol-anti-inflammatory-drug-3002130.html>, last visited on Jul. 11, 2017, 2 pages.

Extended European Search Report dated Mar. 27, 2012, for EP Patent Application No. 09751525.8, filed on May 20, 2009, 7 pages.

FDA Anesthetic and Life Support Drugs Advisory Committee (May 7, 2008). "AQUAVAN® (Fospropofol Disodium) Injection," Web Slide Presentation, 150 pages.

Grosios, K. et al. (1999). "In vivo and in vitro evaluation of combretastatin A-4 and its sodium phosphate prodrug", British Journal of Cancer, 81(8):1318-1327.

Hadzimichalis, N. M. et al. (Dec. 2007, e-pub. Oct. 5, 2007). "Acetaminophen-Mediated Cardioprotection via Inhibition of the Mitochrondrial Permeability Transition Pore-Induced Apoptotic Pathway," Am. J. Physiol. Heart Circ. Physiol. 293:H3348-H3355.

International Search Report dated Dec. 3, 2012, for PCT Patent Application No. PCT/US2012/056625, internationally filed on Sep. 21, 201, 3 pages.

International Search Report dated Jul. 16, 2009, for PCT Patent Application No. PCT/US09/44743, filed on May 20, 2009, 1 page.

International Search Report dated Jul. 7, 2009, for PCT Patent Application No. PCT/US09/44746, filed on May 20, 2009, 1 page.

Kaiyuan (ed.) (2007). "Guidelines and Practice of the Foundation Learning in Nursing," (Apr. 30, 2007). First Edition, P. Kaiyuan ed., Second Military Medical University Press, p. 28.

Kazlauskas, R.J. et al. (1985). "Synthesis of Methoxycarbonyl Phosphate, a New Reagent Having High Phosphoryl Donor Potential for Use in ATP Cofactor Regeneration," J. Org. Chem. 50:1069-1076.

Krise, J.P. et al. (Aug. 12, 1999, e-pub. Jul. 17, 1999). "Novel Prodrug Approach for Tertiary Amines: Synthesis and Preliminary Evaluation of N-Phosphonooxymethyl Prodrugs," Journal of Medicinal Chemistry 42(16):3094-3100.

Laird, B. et al. (May 2008, e-pub. Apr. 23, 2008). "Management of Cancer Pain: Basic Principles and Neuropathic Cancer Pain," European Journal of Cancer 44(8):1078-1082.

Lee, T. et al. (Oct. 2, 2006). "Solubility, Polymorphism, Crystallinity, and Crystal Habit of Acetaminophen and Ibuprofen by Initial Solvent Screening," Pharmaceutical Technology, located at <http://license.icopyright.net/user/viewFreeUse.act?fuid=MTI5NDI0MzY%3D >, last visited on May 26, 2011, 16 pages.

Maharaj, H. et al. (2006, e-pub. Jul. 20, 2006). "Acetylsalicylic Acid and Acetaminophen Protect Against Oxidative Neurotoxicity," Metabolic Brain Disease 21(2-3):189-199.

Mantyla et al. (2002). "A Novel Synthetic Route for the Preparation of Alkyl and Benzyl Chloromehtyl Phosphates," Tetrahedron Letters, 43:3793-3794.

Mayo Clinic (updated Jul. 13, 2013). "Myocardial Ischemia Prevention," located at http://www.mayoclinic.com/health/myocardial-ischemia/DS01179/DSECTION=prevention, last visited on Oct. 29, 2013, two pages.

Mercola. (2017). "The Limits of Tylenol for Pain Relief," located at <http://articles.mercola.com/sites/articles/arccive/2015/04/16/tylenol-acetaminophen-pain-relief.aspx>, last visited on Jul. 11, 2017, 11 pages.

Moller, P.L. et al. (2005). "Intravenous Acetaminophen (Paracetamol): Comparable Analgesic Efficacy, but Better Local Safety than Its Prodrug, Propacetamol, for the Postoperative Pain After Third Molar Surgery," Anesth. Analg. 101:90-96.

Moller, P.L. et al. (2005, e-pub. Mar. 24, 2005). "Onset of Acetaminophen Analgesia: Comparison of Oral and Intravenous Routes After Third Molar Surgery," British Journal of Anaesthesia 94(5):642-648.

Peeters, M.Y. et al. (Mar. 2006). "Propofol Pharmacokinetics and Pharmacodynamics for Depth of Sedation in Nonventilated Infants after Major Craniofacial Surgery" Anesthesiology , 104(3):466-74 http://www.ncbi.nlm.nih.gov/pubmed/16508393.

Poste, G. et al. (1976). "Lipid Vesicles as Carriers for Introducing Biologically Active Materials into Cells," Chapter 4 in Methods in Cell Biology, Prescott, D.M. ed., Academic Press, Inc.: New York, NY, XIV:33-71.

Rautio, J. et al. (2008). "Prodrugs: design and clinical applications", Nature Reviews, 7:255-270.

Roberts II, L.J. et al. (2001). "Analgesic-Antipyretic and Antiinflammatory Agents and Drugs Employed in the Treatment of Gout," Chapter 27 in Goodman & Gillman's the Pharmacological Basis of Therapeutics, 10th Edition, McGraw Hill, Medical Publishing Division: New York, NY, pp. 687-731.

Rowland, M. et al. (1995). "Variability" Chapter 13 in Clinical Pharmacokinetics, Concepts and Applications, Third Edition, p. 207.

Safadi, M. et al. "Phosphoryloxymethyl Carbamates and Carbonates—Novel water-soluble prodrugs for amines and hindered alcohols" Pharmaceutical Research, 10(9):1350-1355.

Sauer, R. et al. (2000). "Water-soluble Phosphate Prodrugs of I-Propargyl-8-styrylxanthine Derivatives, A2A-selective adenosine Receptor Antagonists", J. Med. Chem., 43:440-448.

Shah et al., (2007). "Fospropofol Intravenous Injection for Procedural Sedation: A Population Pharmacokinetic Model" Anesthesiology 107:A45.

Stella, V.J. "Prodrug strategies to overcome poor water solubility", Advanced Drug Delivery Reviews, 59.7(2007) 677-694.

Taniguchi, M. et al. (1981). "Synthesis and Evaluation in Vitro of 4-Acetamidophenyl Phosphate", Chemical and Pharmaceutical Bulletin, 29(2): 577-580.

The China Food and Drug Administration. (Jan. 31, 2011). "CFDA Determines That the Pharmaceutical Preparation Comprising Dextropropoxyphene Will Withdraw From Domestic Market Gradu-

(56) References Cited

OTHER PUBLICATIONS ally," located at <http://www.sda.gov.cn/WS01/CL0051/58315.html>, last visited on Apr. 11, 2014, 4 pages.
U.S. Final Office Action dated Mar. 3, 2015, for U.S. Appl. No. 12/993,088, filed May 29, 2011, 6 pages.
Undevia, S.D. et al. (Jun. 2005). "Pharmacokinetic Variability of Anticancer Agents," Nature Reviews Cancer 5(6):447-458.
Vigroux et a. (1995). "Synthesis of Prodrugs and a Mutual Prodrug of Chlorzoxazone and Acetaminophen Based on a Masked Benzoxazolone," Bioorganic & Medicinal Chemistry Letter, 5(5):427-430.
Wikipedia (last modified Aug. 21, 2013). "Ischemia," located at http://en.wikipedia.org/wiki/Ischemia, last visited on Sep. 11, 2013, 4 pages.
Wikipedia (last modified on Sep. 8, 2013). "Paracetamol," located at http://en.wikipedia.org/wiki/Paracetamol, last visited on Sep. 11, 2013, 19 pages.
Wikipedia. (2017). "Paracetamol," located at < https://en.wikipedia.org/wiki/Paracetamol>, last visited on Jul. 11, 2017, 11 pages.
Written Opinion of the International Searching Authority dated Jul. 7, 2009, for PCT Patent Application No. PCT/US09/44746, filed on May 20, 2009, 5 pages.
Written Opinion of the International Searching Authority dated Jul. 16, 2009, for PCT Patent Application No. PCT/US09/44743, filed on May 20, 2009, 5 pages.
Written Opinion of the International Searching Authority dated Dec. 3, 2012, for PCT Patent Application No. PCT/US2012/056625, Internationally filed on Sep. 21, 2012, 5 pages.

\* cited by examiner

WATER-SOLUBLE ACETAMINOPHEN ANALOGS

CROSS REFERENCE TO RELATED APPLICATIONS

This application is a Continuation of U.S. patent application Ser. No. 15/962,934, filed Apr. 25, 2018, which is a Continuation of U.S. patent application Ser. No. 15/077,802, filed Mar. 22, 2016, now U.S. Pat. No. 9,981,998, issued on May 29, 2018, which is a Continuation of U.S. patent application Ser. No. 12/993,088, which adopts the international filing date of May 20, 2009 and which is a United States national phase application of PCT Application No. PCT/US2009/044743, filed May 20, 2009, and claims priority benefit of U.S. Provisional Application No. 61/054,774, entitled "Water-Soluble Acetaminophen Analogs" filed May 20, 2008, the contents of each of which are hereby incorporated by reference in their entirety as if they were set forth in full below.

BACKGROUND OF THE INVENTION

Acetaminophen (USAN) or paracetamol (INN) (chemically known as N-(4-hydroxyphenyl)acetamide) is an antipyretic and analgesic commonly used to manage fever of any etiology, minor and severe pains (including post-operative pain) and a variety of aches. Acetaminophen is well tolerated and lacks many of the undesired effects of other analgesics, such as non-steroidal anti-inflammatory drugs (NSAIDs) or types of cyclooxygenase (COX) inhibitors (e.g., stomach lining irritation, adverse effects on platelets and renal function, fetal ductus arterious closure complications and Reye's syndrome).

Acetaminophen has also been shown to be effective in protecting tissues from ischemic damage (i.e. damage caused by ischemia as well as reperfusion that follows ischemia). In guinea pigs, acetaminophen was recently found to decrease apoptosis in myocytes, which were subjected to low-flow global myocardial ischemia for 30 minutes followed by 60 minutes of reperfusion (See *Am J Physiol Heart Circ Physiol* 293: H3348-H3355, 2007). In another study, acetaminophen was found to inhibit both lipid peroxidation and superoxide anion generation, resulting in retained structural integrity of the rat hippocampus insulted with quinolinic acid in a cerebral ischemia model (See *Metabolic Brain Disease* 21 (2-3): 180-190, 2006). As with its analgesic applications, an important element of the treatment of ischemic diseases with acetaminophen is the speed at which therapeutic intervention and peak therapeutic blood concentration occurs.

Opioids have gained widespread use in the clinical setting (for example, to control post-operative pain) due to their excellent analgesic properties and onset of action. However, the use of certain opioids is often accompanied by significant adverse side-effects (e.g., respiratory depression, biliary spasm, constipation, sedation, addiction and abuse potential and post-operative nausea and vomiting, etc.) which make them less desirable. The alternative use of NSAIDs, however, impairs blood clotting (in addition to the side effects previously mentioned), which is highly undesirable in post-operative settings which require active wound healing and blood clotting. Due to the undesirable qualities of certain NSAIDs, COX inhibitors, and opioids, particularly in certain clinical settings, there has been a need to develop effective formulations of acetaminophen.

Parenteral formulations of acetaminophen (e.g., intravenous formulations) would be particularly useful in clinical settings. Compared to oral formulations, an acetaminophen parenteral dosage form, such as intravenous bolus or subcutaneous injection, would have various therapeutic advantages. For instance, parenteral acetaminophen may have relatively faster onset of action and ease of administration in settings such as post surgical recovery and trauma. Additionally, as the acetaminophen has a relatively short half-life (about 2 hours; see *Goodman and Gillman's The Pharmacological Basis of Therapeutics* 10$^{th}$ ed, McGraw-Hill 2001, p 704), parenterally-administered acetaminophen may be provided at a lower dosage than oral acetaminophen, since much of the orally-administered acetaminophen is cleared from the body before reaching peak blood concentrations.

Despite a desire for an acetaminophen dosage form suitable for parenteral administration, development of effective therapeutic acetaminophen beyond oral dosage forms has been limited. A major barrier to developing a parenteral dosage form has been acetaminophen's low water solubility (about 1.3 g per 100 mL). To address acetaminophen's inherent solubility, U.S. Pat. No. 4,322,410 discloses a novel water soluble phosphate derivative of acetaminophen (4-acetamidophenyl dihydrogen phosphate), which has a reported water solubility of 50 g per 100 mL of water. However, this acetaminophen derivative is reportedly not readily amenable to chemical and/or enzymatic hydrolysis (and thus not amenable to clinical use) as it requires alkaline phosphatase and about 15 hours in vitro to yield the desired acetaminophen drug from the derivative (see *Chemical and Pharmaceutical Bulletin* 29 (2): 577-580, 1981). Other phosphate-containing prodrugs have been disclosed in, for example, U.S. Pat. Nos. 4,322,410; 5,985,856; 6,204,257; 6,451,776; 6,872,838; and 7,244,718; and U.S. patent application Ser. No. 11/999,660 (US2008/0318905), filed Dec. 5, 2007.

An ester prodrug of acetaminophen, Propacetamol® (4-acetamidophenyl 2-(diethylamino)acetate) was developed in Europe and was later shown to have an inferior local tolerance profile when compared to acetaminophen (90% vs 52%, *British Journal of Anaesthesia* 94 (5): 642-648, 2005; 49% vs 0%, *Anesthesia and Analgesia* 101; 90-96, 2005). Another acetaminophen product marketed in Europe, Perfalgan®, is a large-volume (100-mL) intravenous formulation of acetaminophen for infusion over a relatively long period (about 15 minutes). These products are not optimal clinical solutions either because of their tolerance profile or administration requirements.

Thus, there is still a clear unmet need for improved acetaminophen type drugs, such as an acetaminophen prodrug, which are suitable for small-volume parenteral administration.

The disclosures of all publications, patents, patent applications and other references referred to herein are hereby incorporated herein by reference in their entireties.

BRIEF SUMMARY OF THE INVENTION

One aspect of the present invention provides a compound of the formula (I):

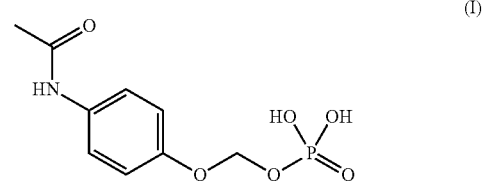 [SMILES: CC(=O)Nc1ccc(OCOP(=O)(O)O)cc1]

or a pharmaceutically acceptable salt thereof or solvate of the foregoing. In some embodiments, the compound is in the form of a disodium salt or solvate thereof.

In some embodiments, the invention embraces a formulation comprising the compound of formula (I) and a carrier. In some embodiments, the formulation comprises an effective amount of the compound of formula (I) and a carrier. In some of these embodiments, the carrier is a pharmaceutically acceptable carrier, such as a carrier that is amenable to parenteral administration.

In some embodiments, the invention embraces a formulation comprising the compound of formula (I) and an opioid, a non-steroidal anti-inflammatory drug (NSAID), a benzodiazepine, and/or a barbiturate. In some embodiments, the invention embraces a formulation comprising the compound of formula (I) and codeine, morphine, hydrocodone, hydromorphone, levorphanol, aspirin, ketorolac, ibuprofen, naproxen, caffeine, tramadol, dextropropoxyphene, methylhexital, diazepam, lorazepam, midazolam, propoxyphene, ketoprofen, flurbiprofen, etodolac, diclofenac, misoprostol, meloxicam, piroxicam, doxylamine, pamabrom, carisoprodol, and/or butalbital.

In some embodiments, the invention embraces a substantially pure form of the compound of formula (I).

In another aspect, the present invention provides methods of treating a disease or condition that is responsive to acetaminophen (e.g., pain, fever, inflammation, ischemic injury (such as myocardial and/or cerebral), neuronal injury, etc.) comprising administering to an individual an effective amount of the compound of formula (I) or a pharmaceutically acceptable salt thereof or solvate of the foregoing. In some embodiments of the method, the compound is administered parenterally. In some embodiments, the compound is administered intravenously. In some embodiments, the compound is administered intramuscularly. In some embodiments, the compound is administered subcutaneously.

In another aspect, the present invention provides methods of treating a disease or condition that is responsive to acetaminophen (e.g., pain, fever, inflammation, ischemic injury (such as myocardial and/or cerebral), neuronal injury, etc.) comprising administering to an individual a formulation of the compound of formula (I) or a pharmaceutically acceptable salt thereof or solvate of the foregoing.

In another aspect, the present invention provides methods of delaying the onset of acetaminophen action in an individual, the methods comprising administering to the individual an effective amount of an effective amount of the compound of formula (I) or a pharmaceutically acceptable salt thereof or solvate of the foregoing, wherein the compound provides a slower onset of acetaminophen action as compared to acetaminophen.

In another aspect, the present invention provides methods of prolonging acetaminophen activity in an individual, the methods comprising administering to the individual an effective amount of the compound of formula (I) or a pharmaceutically acceptable salt thereof or solvate of the foregoing, wherein the compound provides prolonged acetaminophen activity as compared to acetaminophen.

In some embodiments, the compound of formula (I) is administered in a dosage of about 300 mg to about 2.6 g. In other embodiments, the compound is administered in a dosage about 1.3 g to about 1.9 g. In some of these embodiments, the volume of the dosage is about 1-25 mL. In some of these embodiments, the volume of the dosage is about 10-20 mL. In some embodiments, the volume of the dosage is about 1-10 mL. In some embodiments, the volume of the dosage is about 5-10 mL. In some of these embodiments, the dosage is administered more than once a day. In other embodiments, the dosage is administered once every other day or less.

In another aspect, methods of administering low volume/high concentration formulations are provided where the formulations comprise a compound of formula (I) and wherein the compound exhibits enhanced solubility (e.g., water solubility) as compared to the solubility of the acetaminophen. Low volume/high concentration formulations are also provided herein, such as formulations comprising a compound of formula (I) and a pharmaceutically acceptable carrier. A "low volume/high concentration" formulation intends a formulation comprising a carrier and prodrug where a given volume of carrier contains a higher molar concentration of prodrug than is available or obtainable using acetaminophen. Taking the compound of formula (I) as an example, a low volume/high concentration of such prodrug intends a formulation comprising a carrier and the prodrug wherein the formulation contains a higher molar concentration of prodrug in a given volume of carrier than is available or obtainable using acetaminophen. Methods of providing low volume/high concentrations of acetaminophen are also provided comprising administering to an individual a low volume/high concentration formulation of a prodrug as detailed herein (e.g., a prodrug of formula (I) or a salt thereof or solvate of the foregoing). In one aspect, the methods entail administering a prodrug that results in rapid release of acetaminophen when administered to an individual (e.g., by enzymatic cleavage or hydrolysis). Also provided are methods of providing a single dose of acetaminophen in an amount that exceeds currently available doses by administering a prodrug as detailed herein.

In another aspect is provided the use of a compound of formula (I) or a pharmaceutically acceptable salt thereof or solvate of the foregoing for the manufacture of a medicament for the treatment of a condition responsive to acetaminophen. In another aspect is provided the use of a compound of formula (I) or a pharmaceutically acceptable salt thereof or solvate of the foregoing for the treatment of a condition responsive to acetaminophen. In some variations, the condition is pain, fever, inflammation, ischemic injury, or neuronal injury.

In another aspect, the present invention provides a kit comprising the compound of formula (I) or a pharmaceutically acceptable salt thereof or solvate of the foregoing, and instructions for use. In some embodiments, the instructions relate to the use of the compound of formula (I) for the treatment or prevention of a disease or condition that is responsive to acetaminophen (e.g., pain, fever, inflammation, ischemic injury (such as myocardial and/or cerebral), or neuronal injury.

In another aspect, the present invention provides a kit comprising a formulation of the compound of formula (I) and instructions for use. In some embodiments, the instructions relate to the use of the compound of formula (I) for the treatment or prevention of a disease or condition that is responsive to acetaminophen (e.g., pain, fever, inflammation, ischemic injury (such as myocardial and/or cerebral), or neuronal injury).

DETAILED DESCRIPTION OF THE INVENTION

Figure 1:
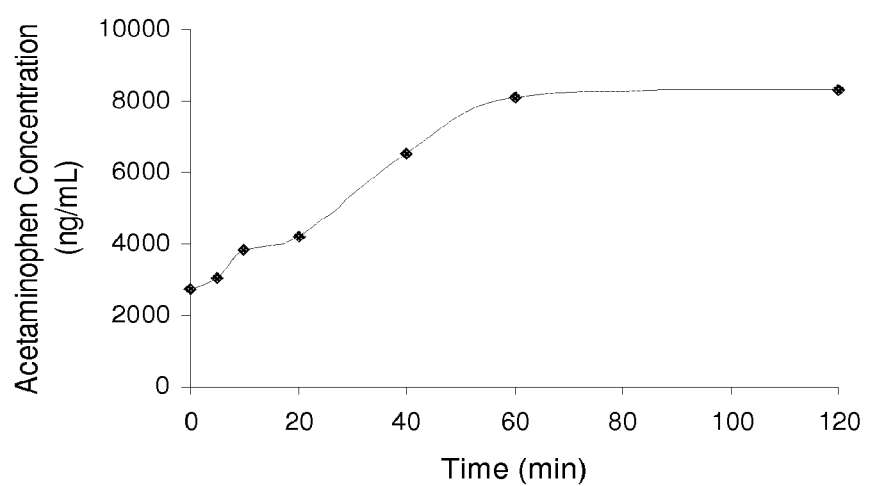
FIG. 1 shows the formation of acetaminophen from 15 µg/mL prodrug in human plasma.

The present invention provides acetaminophen prodrugs which have one or more improved properties (such as increased water solubility and/or onset of action) over existing therapies, which make them potentially useful in low-volume/high-concentration parenteral administration, e.g., intravenous injections. These compounds may be particularly suitable for rapid treatment of a disease or condition that is responsive to acetaminophen, such as pain, fever, inflammation, ischemic injury (such as myocardial and/or cerebral), or neuronal injury.

Accordingly, the present invention in one aspect provides the acetaminophen prodrug, (4-acetamidophenoxy)methyl phosphate, or a pharmaceutically acceptable salt thereof or solvate of the foregoing.

In another aspect, the present invention provides methods of treating a disease or condition that is responsive to acetaminophen (e.g., pain, fever, inflammation, ischemic injury (such as myocardial and/or cerebral), or neuronal injury, etc.) using the acetaminophen prodrugs described herein.

Also provided are kits, formulations, and unit dosage forms of the prodrug.

Abbreviations and Definitions

Nomenclature of some compounds described herein may be identified using ChemDraw Ultra Version 10.0, available from CambridgeSoft®.

The term "prodrug" refers to a compound which provides an active compound following administration to the individual in which it is used, by a chemical and/or biological process in vivo (e.g., by hydrolysis and/or an enzymatic conversion). The prodrug itself may be active, or it may be relatively inactive, then transformed into a more active compound. The invention embraces prodrugs of acetaminophen as described herein.

As used herein, "delaying the onset" or "delayed onset" refers to the increased time to onset of action provided by an acetaminophen prodrug as compared to administration of the molar equivalent of acetaminophen within the same time period through the same route of administration. For example, the delayed release of acetaminophen from the prodrug (4-acetamidophenoxy)methyl dihydrogen phosphate may result in delayed systemic exposure to acetaminophen as compared to administration of the molar equivalent of acetaminophen to an individual.

As used herein, "prolonging activity" or "prolonged activity" refers to the sustained action provided by an acetaminophen prodrug by virtue of the time required to release or otherwise generate acetaminophen from the prodrug. For example, administration of the acetaminophen prodrug (4-acetamidophenoxy)methyl dihydrogen phosphate may result in sustained release of acetaminophen as compared to administration of the molar equivalent of acetaminophen over the same time period through the same route of administration. "Sustained release" refers to release of the acetaminophen, at a rate such that the blood concentration of the acetaminophen (or metabolite thereof) in an individual is maintained at or within the therapeutic range (e.g., above the minimum effective analgesic concentration but below toxic levels) for an extended duration. The extended duration in this context intends any time greater than the time that the molar equivalent of corresponding acetaminophen, administered through the same route, results in an acetaminophen (or metabolite thereof) blood concentration within the therapeutic range.

"Protecting group" refers to a chemical group that exhibits the following characteristics: 1) is stable to the projected reactions for which protection is desired; 2) is removable from the protected substrate to yield the desired functionality; and 3) is removable by reagents compatible with the other functional group(s) present or generated in such projected reactions. Selection of suitable protecting groups for use in the methods described herein is within the ordinary skill level in the art. Examples of suitable protecting groups can be found in Greene et al. (2006) PROTECTIVE GROUPS IN ORGANIC SYNTHESIS, 4th Ed. (John Wiley & Sons, Inc., New York), the content of which is incorporated by reference herein. A "hydroxy protecting group" as used herein denotes a group capable of protecting a free hydroxy group to generate a "protected hydroxyl" which, subsequent to the reaction for which protection is employed, may be removed without disturbing the remainder of the compound. Exemplary hydroxy protecting groups include, but are not limited to, ethers (e.g., allyl, triphenylmethyt (trityl or Tr), benzyl, p-methoxybenzyl (PMB), p-methoxyphenyl (PMP)), acetals (e.g., methoxymethyl (MOM), 3-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Troc), 2-trimethylsilylethyl carbonate), silyl ethers (e.g., trimethylsilyl (TMS), triethylsilyl (TES), triisopropylsilyl (TI PS), triphenylsilyl (TPS), tert-butyldimethylsilyl (TBDMS), tert-butyldiphenylsilyt (TBDPS) and the like.

As used herein, "treatment", "treating", or "treat" is an approach for obtaining beneficial or desired results, including clinical results. For purposes of this invention, beneficial or desired results include, but are not limited to, one or more of the following: decreasing one or more symptoms of a disease or condition that is responsive to acetaminophen, diminishing the extent of the disease or condition, stabilizing the disease or condition (e.g., preventing or delaying the worsening of the disease or condition), delaying or slowing the progression of the disease or condition, ameliorating the disease state or condition, decreasing the dose of one or more other medications required to treat the disease or condition, and increasing the quality of life of an individual who has been or is suspected of having a disease or condition that is responsive to acetaminophen. The disease or condition may be one that is or is believed to be responsive to acetaminophen (e.g., a disease or condition that is accompanied by a fever and/or pain). The disease or condition may be accompanied by inflammation. The disease or condition may be ischemic injury. The disease or condition may be a neuronal injury. In one variation the condition is post-surgical pain and/or fever. In some embodiments, the acetaminophen prodrug and/or formulation comprising the acetaminophen prodrug reduces the severity of one or more symptoms associated with a disease or condition that is responsive to acetaminophen by at least about any of 10%, 20%, 30%, 40%, 50%, 60%, 70%, 80%, 90%, 95%, or 100% compared to the corresponding symptom in the same subject prior to treatment or compared to the corresponding symptom in other subjects not receiving the acetaminophen prodrug and/or formulation. "Responsive to acetaminophen" as used herein refers to a disease or condition, and/or symptom of a disease or condition which may be treated with acetaminophen.

As used herein, "delaying" means to defer, hinder, slow, retard, stabilize, and/or postpone development of the disease or condition that is responsive to acetaminophen, and/or one or more symptoms of a disease or condition that is responsive to acetaminophen. This delay can be of varying lengths of time, depending on the history of the disease and/or individual being treated. As is evident to one skilled in the art, a sufficient or significant delay can, in effect, encompass prevention, in that the individual does not develop the disease or condition. A method that "delays" development of a disease or condition that is responsive to acetaminophen is a method that reduces the probability of disease or condition development in a given time frame and/or reduces the extent of the disease or condition in a given time frame, when compared to not using the method. Such comparisons are typically based on clinical studies, using a statistically significant number of subjects.

As used herein, an "at risk" individual is an individual who is at risk of developing a disease or condition that is responsive to acetaminophen (e.g., pain, fever, inflammation, ischemic injury (such as myocardial and/or cerebral), or neuronal injury). An individual "at risk" may or may not have a detectable disease or condition, and may or may not have displayed symptoms associated with a detectable disease or condition prior to the treatment methods described herein. "At risk" denotes that an individual has one or more so-called risk factors, which are measurable parameters that correlate with development of a disease or condition. An individual having one or more of these risk factors has a higher probability of developing the disease or condition than an individual without these risk factor(s).

As used herein, "pharmaceutically acceptable" refers to a material that is not biologically or otherwise undesirable, e.g., the material may be incorporated (e.g., at the time of manufacturing or administration) into a pharmaceutical composition administered to an individual without causing any significant undesirable biological effects or interacting in a deleterious manner with any of the other components of the composition in which it is contained. As used herein, the term "pharmaceutically acceptable carrier," refers to, for example, solvents, stabilizers, pH-modifiers, tonicity modifiers, adjuvants, binders, diluents, etc., known to the skilled artisan that are suitable for administration to an individual (e.g., a human). Combinations of two or more carriers are also contemplated in the present invention. The pharmaceutically acceptable carrier(s) and any additional components, as described herein, should be compatible for use in the intended route of administration (e.g., oral, parenteral) for a particular dosage form. Such suitability will be easily recognized by the skilled artisan, particularly in view of the teaching provided herein. Pharmaceutically acceptable carriers or excipients have preferably met the required standards of toxicological and manufacturing testing and/or are included on the Inactive Ingredient Guide prepared by the U.S. Food and Drug administration.

The term, "effective amount," as used herein refers to an amount that results in a desired pharmacological and/or physiological effect in an individual who has or is suspected of having (e.g., based on symptoms and/or an individual's perceptions/feelings) a disease or condition or who displays one or more of its symptoms. An effective amount may completely or partially prevent the occurrence or recurrence of the disease or condition or symptom thereof and/or may be therapeutic in terms of a partial or complete cure for the disease or condition and/or adverse effect attributable to the disease or condition (e.g., pain). In reference to a disease or condition described herein (e.g., pain), an effective amount may comprise an amount sufficient to, among other things, reduce and/or relieve to some extent one or more of the symptoms associated with a disease or condition that is responsive to acetaminophen (e.g., pain, fever, inflammation, ischemic injury (such as myocardial and/or cerebral), or neuronal injury). In certain embodiments, the effective amount is sufficient to prevent the condition, as in being administered to an individual prophylactically. Effective amount includes the eradication or amelioration of the underlying condition being treated and/or eradication or amelioration of one or more of the symptoms associated with the underlying condition such that the individual reports an improvement in feeling or condition (e.g., decreased pain intensity and/or duration), notwithstanding that the individual may still be afflicted with the underlying disease or condition. Effective amount also includes halting or slowing the progression of the disease or condition, regardless of whether improvement or the disease or condition is realized.

The "effective amount" may vary depending on the composition being administered, the condition being treated/prevented (e.g., the type of pain), the severity of the condition being treated or prevented, the age, body size, weight, and relative health of the individual, the route and form of administration, the judgment of the attending medical or veterinary practitioner (if applicable), and other factors appreciated by the skilled artisan in view of the teaching provided herein. An effective amount may be assessed, for example, by using data from one or more clinical, physiological, biochemical, histological, electrophysiological, and/or behavioral evaluations.

As is understood in the art, an "effective amount" may be in one or more doses, i.e., a single dose or multiple doses may be required to achieve the desired treatment endpoint. An effective amount may be considered in the context of administering one or more additional pharmaceutical agents, and an acetaminophen prodrug may be considered to be given in an effective amount if, in conjunction with one or more additional pharmaceutical agents, one or more desirable or beneficial result(s) may be or are achieved.

When used with respect to methods of treatment and/or prevention and the use of the acetaminophen prodrugs thereof described herein, an individual "in need thereof" may be an individual who has been diagnosed with, previously treated for, and/or suspected of having the disease or condition to be treated. With respect to prevention, the individual in need thereof may also be an individual who is at risk for a disease or condition (e.g., a family history of the condition, life-style factors indicative of risk for the condition, etc.).

In some variations, the individual has been identified as having one or more diseases or conditions, and/or symptoms thereof described herein. Identification of the diseases or conditions and/or symptoms thereof by a skilled physician is routine in the art (e.g., detection of allergies, cold, cough, flu, pain, etc.) and may also be suspected by the individual or others, for example, due to pain, fever, etc.

In some embodiments, the individual has been identified as susceptible to one or more of the diseases or conditions as described herein. The susceptibility of an individual may be based on any one or more of a number of risk factors and/or diagnostic approaches appreciated by the skilled artisan, including, but not limited to, genetic profiling, family history, medical history (e.g., appearance of related conditions), lifestyle or habits.

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children, infants, and preemies. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. In some embodiments, the individual is a non-mammal, including, but not limited to, birds, and the like. The term "individual" does not denote a particular age or sex.

As used herein, "combination therapy" means a first therapy that includes an acetaminophen prodrug in conjunction with a second therapy (e.g., surgery and/or an additional pharmaceutical agent) useful for treating, stabilizing, preventing, and/or delaying the disease or condition. Administration in "conjunction with" another compound includes administration in the same or different composition(s), either sequentially, simultaneously, or continuously, through same or different routes. In one variation, the combination therapy may include an acetaminophen prodrug and acetaminophen. In some embodiments, the combination therapy optionally includes one or more pharmaceutically acceptable carriers or excipients, non-pharmaceutically active compounds, and/or inert substances.

As used herein, the term "additional pharmaceutical agent," refers to an active agent other than the acetaminophen prodrug (e.g., another drug and/or acetaminophen itself) which is administered to elicit a therapeutic effect. The additional pharmaceutical agent(s) may be directed to (1) a therapeutic effect related to the disease or condition that acetaminophen prodrug is intended to treat or prevent (e.g., pain), (2) treat or prevent a symptom of the underlying condition, (3) reduce the appearance or severity of side effects of administering the acetaminophen prodrug, and/or (4) a therapeutic effect related to a disease or condition that is not responsive to acetaminophen or is relatively less responsive to acetaminophen (e.g., insomnia, anxiety, depression, inflammation, nausea, and/or vomiting).

Reference to "about" a value or parameter herein includes (and describes) variations that are directed to that value or parameter per se. For example, a description referring to "about X" includes the description of "X".

As used herein and in the appended claims, the singular forms "a," "or," and "the" include plural referents unless the context clearly dictates otherwise. It is understood that aspect and variations of the invention described herein include "consisting" and/or "consisting essentially of" aspects and variations.

Unless defined otherwise or clearly indicated by context, all technical and scientific terms and abbreviations used herein have the same meaning as commonly understood by one of ordinary skill in the art to which this invention belongs.

Acetaminophen Prodrugs

The invention embraces acetaminophen prodrugs which may be useful in the treatment of a disease or condition that is responsive to acetaminophen. In some embodiments, the acetaminophen prodrugs contain a phosphate group linked to the acetaminophen hydroxyl group via a linker. In some embodiments, the linker is an alkylene linker (e.g., methylene). In some embodiments of the present invention, the acetaminophen prodrug is of the formula:

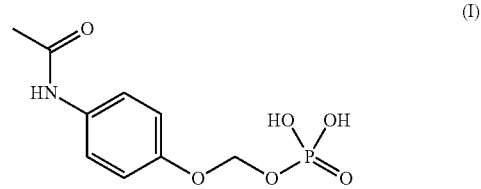 [SMILES: CC(=O)Nc1ccc(OCOP(=O)(O)O)cc1]

(I)

In some embodiments, the acetaminophen prodrug is of the formula:

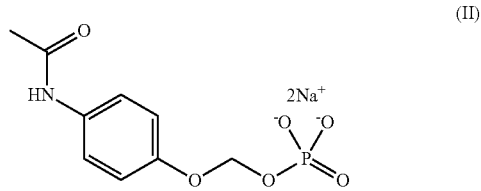

(II)

In some embodiments, the acetaminophen prodrug is in substantially pure form. Unless otherwise stated, "substantially pure" intends a preparation of the prodrug that contains no more than 15% impurity, wherein the impurity denotes compounds other than the acetaminophen prodrug and acetaminophen alone, but does not include acetaminophen and/or other forms or the prodrug (e.g., different salt or non-salt versions of the prodrug). In one variation, a preparation of substantially pure prodrug is provided wherein the preparation contains no more than 25% impurity, or no more than 20% impurity, or no more than 10% impurity, or no more than 5% impurity, or no more than 3% impurity, or no more than 1% impurity, or no more than 0.5% impurity.

The invention also embraces all of the solvate, hydrate and/or salt (e.g., pharmaceutically acceptable salt) forms of the acetaminophen prodrugs described herein and methods of using the same. In some embodiments, the acetaminophen prodrugs of the present invention can exist in unsolvated forms as well as solvated forms (i.e., solvates). The acetaminophen prodrugs may also include hydrated forms (i.e., hydrates).

The invention embraces all salts of the compounds described herein, as well as methods of using such salts of the compounds. The invention also embraces all non-salt forms of any salt of a compound described herein, as well as other salts of any salt of a compound named herein. In some embodiments, the salts of the compounds are pharmaceutically acceptable salts. "Pharmaceutically acceptable salts" are those salts which retain the biological activity of the free compounds and which can be administered as drugs or pharmaceuticals to an individual (e.g., a human). In some embodiments, the acetaminophen prodrugs are mono- or di-substituted by alkali metal or alkaline earth metals. In some embodiments, the acetaminophen prodrug is a mono alkaline phosphate salt (e.g., mono sodium phosphate salt). In some embodiments, the acetaminophen prodrug is a di-alkaline phosphate salt (e.g., disodium phosphate salt). The desired salt of a basic functional group of a compound may be prepared by methods known to those of skill in the art by treating the compound with an acid. The desired salt of an acidic functional group of a compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, bismuth salts, and calcium salts; ammonium salts; and aluminum salts. Examples of organic salts of acid compounds include, but are not limited to, procaine, dibenzylamine, N-ethylpiperidine, N,N'-dibenzylethylenediamine, trimethylamine, and triethylamine salts.

In some embodiments, the acetaminophen prodrugs exhibit enhanced solubility when compared to acetaminophen. For instance, the solubility of acetaminophen in water at room temperature is about 13 mg/mL, whereas the solubility of (4-acetamidophenoxy)methyl phosphate and sodium (4-acetamidophenoxy)methyl phosphate in water at room temperature is approximately 145 mg/mL and 160 mg/mL, respectively. In some embodiments, the acetaminophen prodrugs exhibit reduced or no bioactivity or reduced or no affinity for a receptor wherever applicable, when compared to acetaminophen.

The acetaminophen prodrugs described herein may be relatively stable under some conditions (e.g., during storage and/or preparation in a saline solution), while being converted to their parent drugs under other conditions (e.g., following introduction into an in vitro or in vivo system, such as administration into an individual). In some embodiments, the prodrug (e.g., a prodrug of formula I or II at, for example, about 0.3 ng/mL or about 15 ng/mL in plasma, or between about 0.3 ng/mL or about 15 ng/mL in plasma) is capable of greater than 10%, or 15%, or 20%, or 25%, or 30%, or 35%, or 40%, or 45%, or 50%, or 60%, or 75% conversion to acetaminophen after about any of 1 min, 5 min, 10 min, 15 min, 20 min, or 30 min, or 45 min, or 1 hr at 37° C. In some embodiments, the prodrug (e.g., a prodrug of formula I or II at, for example, about 0.3 ng/mL or about 15 ng/mL in human plasma, or between about 0.3 ng/mL or about 15 ng/mL in human plasma) is capable of greater than about 30%, or about 45% conversion to acetaminophen after about 1 hr at 37° C. In some of these embodiments, the acetaminophen prodrugs are not capable of said conversion to acetaminophen in water, propylene glycol and/or saline at room temperature. For example, in some of these embodiments, the prodrug is not capable of more than any of about 5%, or 10%, or 20%, or 25%, or 30% or 40%, or 60%, or 70% conversion to parent drug at 30 min or 60 min in water or propylene glycol at room temperature. In one embodiment, the acetaminophen prodrug of formula I or II at a concentration of about 15 ng/mL in human plasma (or 0.3 ng/mL, or between 0.3 ng/mL and 15 ng/mL) at 37° C. is capable of greater than 30% conversion to the parent drug at 45 min, and is not capable at the same concentration in water at room temperature of more than 30% conversion at 45 min. In some embodiments, the prodrug (e.g., the acetaminophen prodrug of formula I or II) is capable of at least about any one of 10%, 20%, 30%, 40%, 50%, 60%, 70%, 80%, or 90% increased conversion to parent drug in human plasma at 37° C. compared to water at room temperature after the same time of exposure.

Synthetic Methods

The compounds of the invention may be prepared using a number of methods familiar to one of skill in the art. The discussion below is offered to illustrate one method available for use in assembling the compounds of the invention and is not intended to limit the scope of the reactions or reaction sequences and/or conditions that are useful in preparing compounds of the invention.

Target compounds of the invention may be synthesized starting with readily available acetaminophen as shown in Scheme I below.

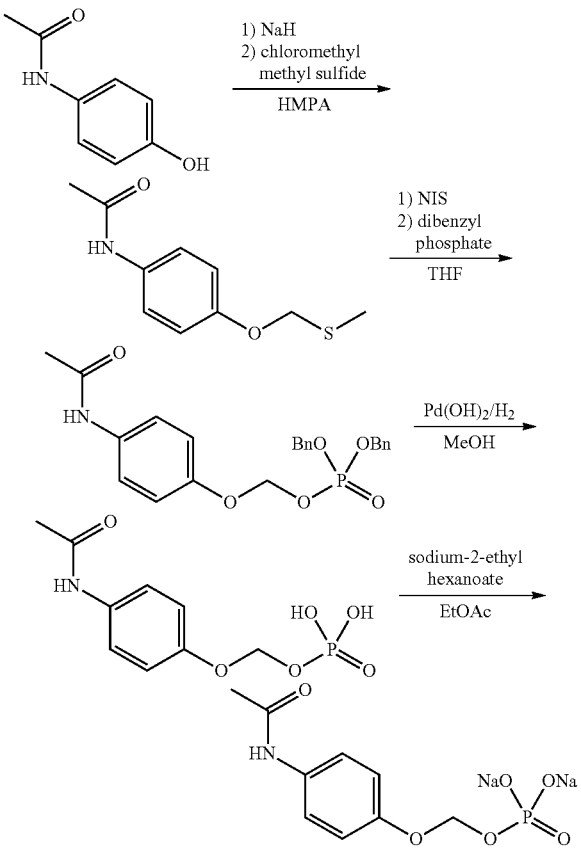

As shown in Scheme I, treatment of acetaminophen with sodium hydride followed by chloromethyl methyl sulfide generates the corresponding thioether, which may be converted to the protected phosphate with the addition of a di-protected phosphate, such as dibenzyl phosphate or di-tert-butyl phosphate, in the presence of a halogenating agent (such as N-iodo succinimide (NIS) or N-bromo succinimide (NBS)). Deprotection under reducing conditions, followed by conversion to the desired salt, such as a sodium salt, results in sodium (4-acetamidophenoxy)methyl phosphate. Any suitable protecting group and accompanying conditions for deprotection may be employed.

The invention also embraces methods of preparing the prodrugs described herein. In one aspect is provided a process for preparing a compound of formula (I):

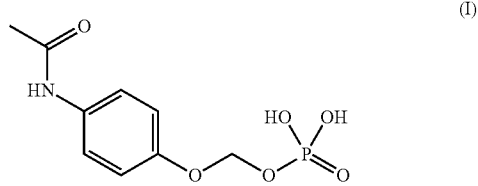

(I)

comprising
(a) reacting a compound of formula SI-A:

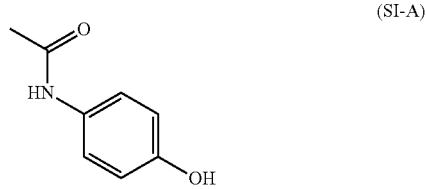

(SI-A)

or a pharmaceutically acceptable salt thereof or solvate of the foregoing, with a halomethyl sulfide in a suitable solvent;
(b) reacting the compound formed from step (a), or a pharmaceutically acceptable salt thereof or solvate of the foregoing, with a di-protected phosphate in a suitable solvent; and
(c) deprotection of the di-protected phosphate of the compound formed from step (b).

In some embodiments of step (a) for the process for preparing a compound of formula I, the halomethyl sulfide is chloromethyl methyl sulfide. In some embodiments of step (a), the suitable solvent is HMPA. In some embodiments of step (a), the reaction further comprises NaH. In some embodiments of step (b) for the process for preparing a compound of formula I, the di-protected phosphate is di-tert-butyl phosphate or dibenzylphosphate. In some embodiments of step (b), the suitable solvent is THF. In some embodiments of step (b), the reaction further comprises NIS or NBS. In some embodiments of step (c) for the process for preparing a compound of formula I, the deprotection comprises reducing conditions. In some embodiments of step (c), the deprotection comprises using Pd(OH)$_2$/H$_2$. In some embodiments of step (c), the deprotection comprises acidic conditions. In some embodiments of step (c), the deprotection comprises treatment with acetic acid. In some embodiments of step (c), the suitable solvent is a protic solvent (e.g., methanol).

Formulations

The acetaminophen prodrugs described herein can be in formulations (including pharmaceutical compositions) with additives such as excipients (e.g., one or more excipients), antioxidants (e.g., one or more antioxidants), stabilizers (e.g., one or more stabilizers), preservatives (e.g., one or more preservatives), pH adjusting and buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents, viscosity-increasing agents (e.g., one or more viscosity-increasing agents), and the like, either alone or together with one or more additional pharmaceutical agents, provided that the additional components are pharmaceutically acceptable for the particular disease or condition to be treated. In some embodiments, the formulation may include combinations of two or more of the additional components as described herein (e.g., 2, 3, 4, 5, 6, 7, 8, or more additional components). In some embodiments, the additives include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in REMINGTON'S PHARMACEUTICAL SCIENCES, Marck Pub. Co., New Jersey 18$^{th}$ edition (1996), and REMINGTON: THE SCIENCE AND PRACTICE OF PHARMACY, Lippincott Williams & Wilkins, Philadelphia, 20$^{th}$ edition (2003) and 21$^{st}$ edition (2005).

The formulations may vary or be tailored according to the condition to be treated, the amount of compound to be administered, the condition of the individual, and other variables that will readily be apparent to one of ordinary skill in the art in view of the teachings provided herein.

In some embodiments, the formulation (e.g., formulations amenable to parenteral administration) is an aqueous formulation with a pH from about 3.5 to about 9.5, or from about 4.5 to about 8.5, or from about 5.0 to about 9.0, or from about 5.5 to about 8.5, or from about 6.0 to about 8.0, or from about 6.5 to about 8.0, or from about 7.0 to about 8.0, or about 7.4.

Formulations comprising a prodrug of the formula I or II and saline are provided. In one aspect, such formulations are at physiological pH (about 7.4). Such formulations may be amenable to storage and subsequent use with the prodrug remaining intact for prolonged periods of time (e.g., during storage) and converted to acetaminophen after administration to an individual (e.g., an adult, child, or infant). In some embodiments, the prodrug is stored as a dry powder and the formulation is generated by dissolving the dry powder in saline prior to administration. In one aspect, prodrug formulations are provided, e.g., formulations comprising the molar equivalent of about any of 50 mg/mL, 75 mg/mL, 100 mg/mL, 125 mg/mL, 150 mg/mL, 175 mg/mL, or 200 mg/mL of acetaminophen, wherein molar equivalent is the amount of prodrug that would result in the indicated amount of acetaminophen upon complete conversion. For any amount (e.g., dosage) of prodrug described herein, also contemplated is the molar prodrug equivalent for that amount of acetaminophen. Single bolus formulations are also provided, e.g., up to about any of 5 mL, 10 mL, or 15 mL (at, for example, the molar prodrug equivalent of about 1450 mg to about 1600 mg of acetaminophen).

Kits

The invention also provides kits containing materials useful for the treatment or prevention of a condition that is responsive to acetaminophen (e.g., pain). The kits may contain an acetaminophen prodrug of the invention and instructions for use. The kits may comprise a container with a label. Suitable containers include, for example, bottles, vials, and test tubes. The containers may be formed from a variety of materials such as glass or plastic. The containers may hold an acetaminophen prodrug or a formulation of an acetaminophen prodrug (e.g., a formulation further comprising one or more additional pharmaceutical agents). The label on the container may indicate that the acetaminophen prodrug or the formulation is used for treating or suppressing a condition that is responsive to acetaminophen (e.g., pain), and may also indicate directions for either in vivo or in vitro use, such as those described herein.

The invention also provides kits comprising one or more of the acetaminophen prodrugs of the invention. In some embodiments, the kit of the invention comprises the container described above. In other embodiments, the kit of the invention comprises the container described above and a second container comprising a buffer. It may further include other materials desirable from a commercial and user standpoint, including other buffers, diluents, filters, needles, syringes, and package inserts with instructions for performing any methods described herein.

In other aspects, the kits may be used for any of the methods described herein, including, for example, to treat an individual with one or more conditions responsive to acetaminophen (e.g., pain and/or fever), or to suppress one or more such conditions.

In certain embodiments the kits may include a dosage amount of at least one formulation as disclosed herein. In one aspect, dosage forms correspond to dose that exceed the molar equivalent of 4 g/day of acetaminophen. Kits may also comprise a means for the delivery of the formulation thereof.

The kits may include additional pharmaceutical agents for use in conjunction with the formulation described herein. In some variations, the additional pharmaceutical agent(s) may be one or more analgesic drug(s). These agents may be provided in a separate form, or mixed with the compounds of the present invention, provided such mixing does not reduce the effectiveness of either the pharmaceutical agent or formulation described herein and is compatible with the route of administration. Similarly the kits may include additional agents for adjunctive therapy or other agents known to the skilled artisan as effective in the treatment or prevention of the conditions described herein.

The kits may optionally include appropriate instructions for preparation and/or administration of a formulation comprising an acetaminophen prodrug of the invention. Information detailing possible side effects of the formulation, and any other relevant information may also be enclosed. The instructions may be in any suitable format, including, but not limited to, printed matter, videotape, computer readable disk, optical disc or directions to internet-based instructions.

In another aspect of the invention, kits for treating an individual who suffers from or is susceptible to a disease or condition described herein (e.g., pain and/or fever) are provided, comprising a first container comprising a dosage amount of a composition as disclosed herein, and instructions for use. The container may be any of those known in the art and appropriate for storage and delivery of intravenous formulation. In certain embodiments the kit further comprises a second container comprising a pharmaceutically acceptable carrier, diluent, adjuvant, etc. for preparation of the formulation to be administered to the individual.

Kits may also be provided that contain sufficient dosages of the compounds described herein (including formulations thereof) to provide effective treatment for an individual for an extended period, such as 1-3 days, 1-5 days, a week, 2 weeks, 3, weeks, 4 weeks, 6 weeks, 8 weeks, 3 months, 4 months, 5 months, 6 months, 7 months, 8 months, 9 months or more.

The kits may include the composition as described herein packaged in either a unit dosage form or in a multi-use form. The kits may also include multiple units of the unit dose form.

Methods of Treatment

The acetaminophen prodrugs of the present invention may be used to treat a disease or condition that is responsive to acetaminophen (e.g., pain and/or fever). In one embodiment, the invention provides a method of treating a disease or condition that is responsive to acetaminophen comprising administering to an individual an effective amount of an acetaminophen prodrug (e.g., (4-acetamidophenoxy)methyl phosphate or sodium (4-acetamidophenoxy)methyl phosphate). In some embodiments, the individual is at risk of developing a disease or condition that is responsive to acetaminophen. In some embodiments, methods of treating pain, fever, inflammation, ischemic injury (such as myocardial and/or cerebral), or neuronal injury in an individual, comprising administering to the individual an effective amount of an acetaminophen prodrug (e.g., (4-acetamidophenoxy)methyl phosphate or sodium (4-acetamidophenoxy)methyl phosphate) are provided. In one variation, the individual is post-operative and has or is believed to have or developed post-operative pain. In one variation, the prodrug is administered prophylactically for post-operative pain. In one variation, the individual is not amenable to oral administration of acetaminophen.

The invention embraces methods of treating pain of any etiology, including acute and chronic pain, and any pain in which acetaminophen analgesic is prescribed. Examples of pain include post-surgical pain, post-operative pain (including dental pain), migraine, headache and trigeminal neuralgia, pain associated with burn, wound or kidney stone, pain associated with trauma (including traumatic head injury), neuropathic pain (e.g., peripheral neuropathy and post-herpetic neuralgia), pain associated with musculo-skeletal disorders, strains, sprains, contusions, fractures, such as myalgia, rheumatoid arthritis, osteoarthritis, cystitis, pancreatitis, inflammatory bowel disease, ankylosing spondylitis, sero-negative (non-rheumatoid) arthropathies, non-articular rheumatism and peri-articular disorders, and pain associated with cancer (including "break-through pain" and pain associated with terminal cancer). Examples of pain with an inflammatory component (in addition to some of those described above) include rheumatic pain, pain associated with mucositis, and dysmenorrhea. In some variations, the methods and formulations of the present invention are used for treatment or prevention of post-surgical pain and/or cancer pain. In some variations, the methods and compositions of the present invention are used for treatment or prevention of pain that is selected from the group consisting of pain associated with surgery, trauma, osteoarthritis, rheumatoid arthritis, lower back pain, fibromyalgia, postherpetic neuralgia, diabetic neuropathy, HIV-associated neuropathy and complex regional pain syndrome.

In some variations, the methods and compositions of the present invention (e.g., (4-acetamidophenoxy)methyl phosphate or sodium (4-acetamidophenoxy)methyl phosphate) are used for treatment or prevention of pain and/or fever (e.g., in adults, children and/or infants). In some embodiments, the methods and compositions of the present invention (e.g., (4-acetamidophenoxy)methyl phosphate or sodium (4-acetamidophenoxy)methyl phosphate) are used for treatment of pain, such as acute pain (e.g., acute pain following surgery, such as orthopedic surgery of adults, children, and/or infants). In some embodiments, the methods and compositions of the present invention (e.g., (4-acetamidophenoxy)methyl phosphate or sodium (4-acetamidophenoxy)methyl phosphate) are used for treatment or prevention of fever, such as endotoxin-induced fever (e.g., endotoxin-induced fever in adults, children, and/or infants). In some embodiments, the methods and compositions of the present invention (e.g., (4-acetamidophenoxy) methyl phosphate or sodium (4-acetamidophenoxy)methyl phosphate) are used for treatment or prevention of fever in children and/or infants. In some embodiments, the fever is selected from low-grade fever, moderate fever, high-grade fever and hyperpyrexia fever. In some embodiments, the fever is selected from Pel-Eb stein fever, continuous fever, intermittent fever, and remittent fever.

In some embodiments, the invention embraces methods of delaying the onset of acetaminophen action in an individual in need of acetaminophen therapy, the method comprising administering to the individual an effective amount of an acetaminophen prodrug (e.g., (4-acetamidophenoxy)methyl phosphate or sodium (4-acetamidophenoxy)methyl phosphate) wherein the prodrug provides a slower onset of acetaminophen action as compared to acetaminophen. In one variation, administration of the acetaminophen prodrug (e.g., (4-acetamidophenoxy)methyl phosphate or sodium (4-acetamidophenoxy)methyl phosphate) delays the onset of parent drug action by greater than about 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours, or 24 hours as compared to administration of acetaminophen. In some embodiments, the invention embraces little or no delay in the onset of the parent drug.

In some embodiments, the invention embraces methods of prolonging acetaminophen activity in an individual in need of acetaminophen therapy, the method comprising administering to the individual an effective amount of an acetaminophen prodrug (e.g., (4-acetamidophenoxy)methyl phosphate or sodium (4-acetamidophenoxy)methyl phosphate) wherein the prodrug provides prolonged acetaminophen activity as compared to acetaminophen. In one variation, administration of the acetaminophen prodrug (e.g., (4-acetamidophenoxy)methyl phosphate or sodium (4-acetamidophenoxy)methyl phosphate) prolongs activity by greater than about 5 minutes, or 10 minutes, or 15 minutes, or 30 minutes, or 1 hour, or 2, hours, or 3 hours, or 4 hours, or 6 hours, or 8 hours, or 10 hours, or 12 hours, or 18 hours, or 24 hours as compared to administration of the acetaminophen. In some embodiments, the invention embraces little or no prolonging of activity compared to administration of acetaminophen.

In some embodiments, the invention embraces a method of providing acetaminophen to an individual, the method comprising administering an acetaminophen prodrug (e.g., a prodrug of formula I or II), wherein the acetaminophen prodrug converts to acetaminophen. Also provided are methods of providing acetaminophen to an individual by administering an acetaminophen prodrug (e.g., a prodrug of formula I or II), where the prodrug converts to acetaminophen in vivo. In one aspect, the prodrug (e.g., a prodrug of formula I or II) results in conversion to acetaminophen within about 1, 5, 10, 15, or 30 min following administration. Conversion may be measured by techniques known in the art, including those detailed in the Experimental section herein. In some embodiments, the invention embraces methods of providing acetaminophen to an individual (e.g., an individual in need of acetaminophen therapy), the method comprising administering to the individual an effective amount of an acetaminophen prodrug (e.g., a prodrug of formula I or II) wherein greater than about any of 10%, or 15%, or 20%, or 25%, or 30%, or 35%, or 40%, or 45%, or 50%, or 60%, or 75% or 85%, or 90%, or 95% of the prodrug is converted to acetaminophen after less than about any of 1 min, 3 min, 5 min, 10 min, 20 min, or 30 min, or 45 min, or 1 hr following administration. In some embodiments, the method comprises administering to the individual an effective amount of an acetaminophen prodrug (e.g., a prodrug of formula I or II) wherein greater than about 10% or about 20% of the prodrug is converted to acetaminophen after less than about 1 min or about 3 min following administration.

In some embodiments, the invention embraces a method of providing acetaminophen to an individual (e.g., an individual in need of acetaminophen therapy), the method comprising administering to the individual (e.g., intravenously) an effective amount of an acetaminophen prodrug (e.g., a prodrug of formula I or II) wherein the resulting concentration of acetaminophen (e.g., at about any of 10 min, or 20 min, or 30 min, or 45 min, or 1 hr, or 2 hr, or 3 hr following administration) is within less than about any of 50%, or 40%, or 30%, or 25%, or 20%, or 15%, or 10%, or 5% when compared to the administering acetaminophen alone under the same conditions. For example, in some embodiments, a methods of providing acetaminophen to an individual in need of acetaminophen therapy are provided, the methods comprising intravenously administering to the individual an effective amount of an acetaminophen prodrug (e.g., a prodrug of formula I or II) wherein the resulting concentration of acetaminophen or a metabolite thereof (e.g., at about 30 min or 1 hr following administration) is within less than about 15% or about 5% when compared to administering acetaminophen alone under the same conditions.

Combination Therapy

The acetaminophen prodrugs described herein may be formulated and/or administered in conjunction with one or more additional pharmaceutical agents, as described herein and as known in the art, including one or more additional pharmaceutical agents to further reduce the occurrence and/or severity of symptoms and/or clinical manifestations thereof, as well as additional pharmaceutical agents that treat or prevent the underlying conditions, or in conjunction with (e.g., prior to, concurrently with, or after) additional treatment modalities. The acetaminophen prodrugs as described herein may be administered before, concurrently with, or after the administration of one or more of the additional pharmaceutical agents. The acetaminophen prodrugs described herein may also be administered in conjunction with (e.g., prior to, concurrently with, or after) agents to alleviate the symptoms associated with either the condition or the treatment regimen.

In some embodiments of the formulations and methods of the present invention, the acetaminophen prodrugs are used in combination with one or more additional pharmaceutical agents. Representative additional pharmaceutical agents include opioids (natural, semi-synthetic, or synthetic), non-steroidal anti-inflammatory drugs (NSAIDs), benzodiazepines, barbiturates and other compounds, such as caffeine. Examples of compounds contemplated for combination with prodrug of current invention include, but are not limited to, codeine, morphine, hydrocodone, hydromorphone, levorphanol, aspirin, ketorolac, ibuprofen, naproxen, caffeine, tramadol, dextropropoxyphene, methylhexital, diazepam, lorazepam, midazolam, propoxyphene, ketoprofen, flurbiprofen, etodolac, diclofenac, misoprostol, meloxicam, piroxicam, doxylamine, pamabrom, carisoprodol, and butalbital.

One potential advantage of a combination formulation is that the formulation may induce analgesia beyond the ceiling effect of acetaminophen without approaching the toxic or nearly toxic dose levels of acetaminophen. Combinations of the acetaminophen prodrugs with benzodiazepines such as diazepam, lorazepam, midazolam or any other benzodiazepines, may be used for treatment of pre- and postoperative anxiety in addition to the treatment of e.g., analgesia. Such combination may be particularly useful in dental surgeries (e.g., mole extraction).

The above additional pharmaceutical agents to be employed in combination with the acetaminophen prodrugs of the invention may be used in therapeutic amounts, such as those indicated in the PHYSICIANS' DESK REFERENCE (PDR) 53rd Edition (1999), or such therapeutically useful amounts as would be known to one of ordinary skill in the art.

Additional pharmaceutical agents (e.g., analgesic drugs) administered with one or more of the acetaminophen prodrugs of the invention can be administered at the recommended maximum clinical dosage or at lower doses. Dosage levels of the additional pharmaceutical agents in the formulations of the invention may be varied so as to obtain a desired therapeutic response depending on the route of administration, severity of the disease and the characteristics and response of the patient. The combination can be administered as separate formulations or as a single dosage form containing both agents. When administered as a combination, the acetaminophen prodrugs can be formulated as separate formulations, which are given at the same time or different times, or the acetaminophen prodrugs, can be given as a single formulation.

As will be well appreciated by the skilled artisan, for particular conditions, different additional pharmaceutical agent(s) and/or additional treatment modality(ies) may be employed.

In some embodiments, an acetaminophen prodrug of the current invention may be formulated and/or administered with acetaminophen itself. Such combination therapy may provide an initial therapeutic amount of the parent drug, followed by a delayed and/or prolonged parent drug activity from the prodrug. For example, a combination of (4-acetamidophenoxy)methyl dihydrogen phosphate with acetaminophen may provide an initial treatment of pain with acetaminophen, followed by prolonged treatment of pain with the acetaminophen prodrug. Such formulations may permit a decreased dosing frequency. Alternatively, an initial dose of prodrug I or II (e.g., as a low volume, high concentration dose to treat post-operative pain and/or fever) may be followed by administration of acetaminophen to treat pain and/or fever (e.g., after discharge from a hospital or surgical setting).

The formulations and methods described herein may be used alone or in conjunction with (e.g., prior to, concurrently with, or after) other modes of treatments (e.g., adjunctive therapy with additional pharmaceutical agents described herein with reference to pharmaceutical formulations of the claimed compounds or known to the skilled artisan) used to treat or prevent the condition being treated/prevented and/or administration of an additional treatment modality, or combinations of the foregoing). For example, in combination with one or more additional pharmaceutical agents as described herein and known to those of skill in the art and/or currently available treatment modalities, including, for example, surgery or radiotherapy. As used herein, the term "additional treatment modality" refers to treatment/prevention of the conditions described herein without the use of a pharmaceutical agent (e.g., surgery, radiotherapy, etc.). Where combinations of pharmaceutical agent(s) and/or additional treatment modality(ies) are used, they may be, independently, administered prior to, concurrently with, or after administration of one or more of the acetaminophen prodrugs (or formulation(s) thereof) as described herein.

The optimal combination of one or more additional treatment modalities and/or additional pharmaceutical agents in conjunction with administration of the formulations described herein, can be determined by an attending physician or veterinarian based on the individual and taking into consideration the various factors effecting the particular individual, including those described herein.

Dosing and Methods of Administration

The acetaminophen prodrugs and formulations described herein will generally be used in an amount effective to achieve the intended result, for example in an effective amount to treat or prevent the particular condition being treated or prevented (e.g., pain and/or fever). The amount of the acetaminophen prodrug or formulation administered in order to administer an effective amount will depend upon a variety of factors, including, for example, the particular condition being treated, the frequency of administration, the particular formulation being administered, the severity of the condition being treated and the age, weight and general health of the individual, the adverse effects experienced by the individual being treated, etc. Determination of an effective dosage is within the capabilities of those skilled in the art, particularly in view of the teachings provided herein. Dosages may also be estimated using in vivo animal models.

The amount of acetaminophen prodrug that may be combined with the carrier materials to produce a single dosage form may vary depending upon the host to which the acetaminophen prodrug is administered and the particular mode of administration, in addition to one or more of the variety of factors described above. A pharmaceutical unit dosage chosen may be fabricated and administered to provide a defined final concentration of drug in the blood, tissues, organs, or other targeted region of the body. The effective amount for a given situation can be readily determined by routine experimentation and is within the skill and judgment of the ordinary clinician.

In some embodiments, the dosage of acetaminophen prodrug required to obtain the same blood level concentration as acetaminophen is lower due to the increased solubility of the prodrug. In some embodiments, the required dosage of the prodrug to obtain the same blood level concentration as the acetaminophen is 1.2, 2, 5, 7.5, 10, 15, 20, 50, or 100 times lower than acetaminophen.

Examples of acetaminophen prodrug dosages (alone or in combination) which can be used are an effective amount within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight. Compounds of the present invention may be administered, alone or in combination, in a single daily dose, or the total daily dosage may be administered in divided dosage of two, three, four, five, or six times daily.

The frequency and duration of administration of the acetaminophen prodrug will depend on the condition being treated, the condition of the individual, and the like. The formulation may be administered to the individual one or more times, for example, 2, 3, 4, 5, 10, 15, 20, or more times. The formulation may be administered to the individual, for example, more than, equal to, or less than once a day, 2 times a day, 3 times a day, or more than 3 times a day; or 1-6 times a day, 2-6 times a day, or 4-6 times a day. The formulation may also be administered to the individual, for example, less than once a day, for example, every other day, every third day, every week, or less frequently. The formulation may be administered over a period of days, weeks, or months.

The acetaminophen prodrugs of the invention may be administered enterally (e.g., orally or rectally), parenterally (e.g., by injection (such as intravenously or intramuscularly), or by inhalation (e.g., as mists or sprays), or topically, in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g., via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques. The acetaminophen prodrugs may be mixed with pharmaceutically acceptable carriers, adjuvants, and vehicles appropriate for the desired route of administration. The route of administration may vary according to the condition to be treated. Additional methods of administration are known in the art.

In some embodiments of the methods, the route of administration is oral. In some embodiments, formulations are suitable for oral administration. The acetaminophen prodrugs described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such formulations may also comprise adjuvants, such as wetting agents, emulsifying and suspending agents, cyclodextrins, and sweetening, flavoring, and perfuming agents.

In some embodiments, the acetaminophen prodrug is administered parenterally (e.g., intravenously or intramuscularly). Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. The sterile injectable preparation may also be a sterile powder to be reconstituted using acceptable vehicles prior to administration. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the preparation of injectables.

In some embodiments are provided high doses of acetaminophen prodrug in a low volume (e.g., in a low volume of saline). Non-limiting examples of an effective amount (e.g., for parenteral administration, such as intravenous or intramuscular), include the acetaminophen prodrug at a dosage range of from about 20 mg per day to about 8 g per day, or from about 60 mg per day to about 6 g, or from about 200 mg per day to about 4 g, or from about 300 mg to about 2.6 g per day, or from about 500 mg to about 2 g per day. In some embodiments, the effective amount for parenteral (e.g., intravenous or intramuscular) administration is a dose volume of about 200 mg to about 5 g, or about 500 mg to about 4 g, or about 750 mg to about 3 g, or about 1 g to about 2.5 g, or about 1.3 g to about 1.9 g, in about 1 mL to about 30 mL, or about 1 mL to about 25 mL, or about 5 mL to about 20 mL, or about 5 mL to about 15 mL or about 10 mL to about 15 mL, or about 5 mL to about 10 mL. In some of these embodiments, the acetaminophen prodrug is administered in a solution at a concentration of about 10 mg/mL to about 1000 mg/mL, or about 25 mg/mL to about 750 mg/mL, or about 50 mg/mL to about 500 mg/mL, or about 75 mg/mL to about 400 mg/mL, or about 100 mg/mL to about 300 mg/mL, or about 150 mg/mL to about 250 mg/mL.

The invention also includes formulations of acetaminophen prodrugs administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The acetaminophen prodrugs of the present invention may also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and/or metabolizable lipid capable of forming liposomes may be used. The present formulations in liposome form can contain, in addition to an acetaminophen prodrug, stabilizers, preservatives, excipients, and the like. In some embodiments, the lipids are the phospholipids and/or phosphatidyl cholines (lecithins), natural and/or synthetic. Methods to form liposomes are known in the art. See, for example, Prescott, Ed., Methods in Cell Biology, Volume XIV, Academic Press, New York, N.W., p. 33 et seq (1976).

EXAMPLES

The present invention will be understood more readily by reference to the following examples, which are provided by way of illustration and are not intended to be limiting of the present invention.

Example 1: Synthesis of (4-acetamidophenoxy)methyl dihydrogen phosphate

N-(4-(methylthiomethoxy)phenyl)acetamide

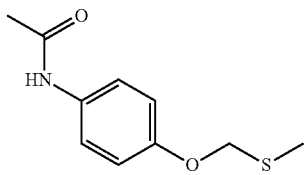

To a stirred ash-colored suspension of sodium hydride (1.9 g; 75.49 mmol) in hexamethylphosphoramide (HMPA; 25 mL) cooled to 0° C., a solution of acetaminophen (10 g; 66.22 mmol in 35 mL of HMPA) was added slowly in about 15 minutes. The ash-colored suspension changed to a light-brown clear solution after 15 minutes of stirring. The reaction mixture was stirred for an additional 20 minutes at 0° C. Then chloromethyl methyl sulfide (7.67 g; 79.47 mmol) was slowly added to the reaction mixture over about 10 minutes. There was no color change in reaction mixture. The reaction mixture was slowly warmed to room temperature and stirring continued for 3 hr. $R_f$ values of starting material and product, in a methanol:dichloromethane solvent system (3:97) on TLC silica gel 60 $F_{254}$ (Merck) detected at λ254 nm, were 0.4, and 0.6, respectively. The reaction mixture was quenched with saturated ammonium chloride solution (80 mL), extracted with ethyl acetate (2×75 mL), the light-brown organic layer separated, dried over sodium sulphate and concentrated under vacuum. The crude light-brown compound was purified by washing with hexane (3×50 mL), acetonitrile (15 mL), diethyl ether (100 mL), and a white solid N-(4-(methylthiomethoxy) phenyl)acetamide product was obtained (3.5 g, 25% yield).

(4-acetamidophenoxy)methyl dibenzyl phosphate

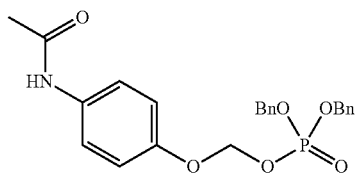

To a stirred colorless solution of N-(4-(methylthiomethoxy)phenyl)acetamide (1.5 g; 7.1 mmol) in THF (stirred with 5 g of activated 4 Å molecular sieves for 15 minutes), was added a brown colored suspension of N-iodo succinimide (2.6 g; 10.7 mmol) followed by addition of dibenzyl phosphate (3.1 g; 11.14 mmol) dissolved in DCM. The resulting brown colored reaction mixture was stirred at room temperature for 2 hours. $R_f$ values of starting material, dibenzyl phosphate, and product in methanol:dichloromethane solvent system (3:97) on TLC silica gel 60 $F_{254}$ (Merck) detected at A, 254 nm were 0.6, 0.2, and 0.5, respectively. The reaction mixture was filtered with Whatman filter paper and the brown filtrate was washed with water (20 mL), extracted with dichloromethane (50 mL), the organic layer separated, washed with 20% sodium thiosulphate (2×50 mL) and 10% sodium bicarbonate (30 mL), dried with sodium sulphate, and evaporated to yield the product (1.9 g, 60% yield) as a brown color viscous liquid which was purified by column chromatography (silica gel), using 5% methanol in dichloromethane as an eluent.

(4-acetamidophenoxy)methyl dihydrogen phosphate

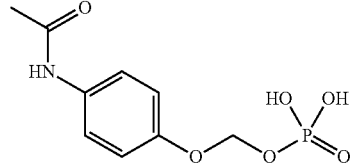 [SMILES: CC(=O)Nc1ccc(OCOP(=O)(O)O)cc1]

To a stirred brown colored solution of (4-acetamidophenoxy)methyl dibenzyl phosphate (0.4 g 0.9 mmol) in methanol (15 mL), a solution of Pd(OH)$_2$ (0.2 g) in methanol (10 mL) was added. The reaction mixture was taken into a glass vessel kept at 60 psi in a Parr hydrogenator at room temperature. $R_f$ values of starting material and product in a methanol:dichloromethane solvent system (10:90) on TLC silica gel 60 $F_{254}$ (Merck) detected at λ 254 nm were 0.0, and 0.5, respectively. The catalyst was filtered through celite and washed with methanol (3×5 mL). The filtrate was concentrated under vacuum to produce a brown colored gummy mass which was then purified by washing with pentane (2×50 mL) and diethyl ether (30 mL) to yield 50 mg (30% yield) of product as an off white solid (melting range: 109-111° C.). $^1$H NMR (400 MHz, DMSO-d$_6$): δ 9.82 (s, 1H), 7.48 (d, 2H, J=8.8 Hz), 6.98 (d, 2H, J=8.8 Hz), 5.43 (d, 2H, J=10.0 Hz), 2.50 (s, 3H).

Example 2: Synthesis of Sodium (4-acetamidophenoxy)methyl phosphate

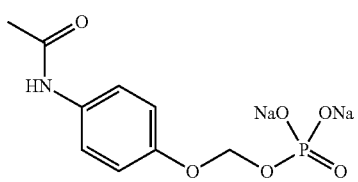

To a stirring milky suspension of (4-acetamidophenoxy) methyl dihydrogen phosphate (20 mg; 0.076 mmol) in ethyl acetate (5 mL), a solution of sodium-2-ethyl hexanoate (25 mg; 0.15 mmol) in ethyl acetate (2 mL) was added. The reaction suspension was stirred for 3 h. The milky suspension turned to a white solid after one hour, which was filtered, washed with ethyl acetate (3×15 mL) and ether (3×20 mL) to yield 10 mg (50% yield) of product as a white solid (melting range: 206-209° C.). $^1$H NMR (400 MHz, DMSO): δ 9.8 (s, 1H), 7.41 (d, 2H, J=10.8 Hz), 6.96 (d, 2H, J=11.6 Hz), 5.26 (d, 2H, J=10.4 Hz), 1.97 (s, 3H).

Example 3: Solubility of Acetaminophen Analogs

Solubility of (4-acetamidophenoxy)methyl dihydrogen phosphate and its disodium salt is listed in Table. 1.

TABLE 1

| Solubility of Acetaminophen Prodrugs | | |
|---|---|---|
| Solute | Solvent | Solubility (mg/mL) |
| (4-acetamidophenoxy)methyl dihydrogen phosphate | Water | 145 |
| Sodium (4-acetamidophenoxy)methyl phosphate | Water | 160 |

Example 4: In Vitro Conversion of Acetaminophen Prodrug to Acetaminophen

Figure 2:
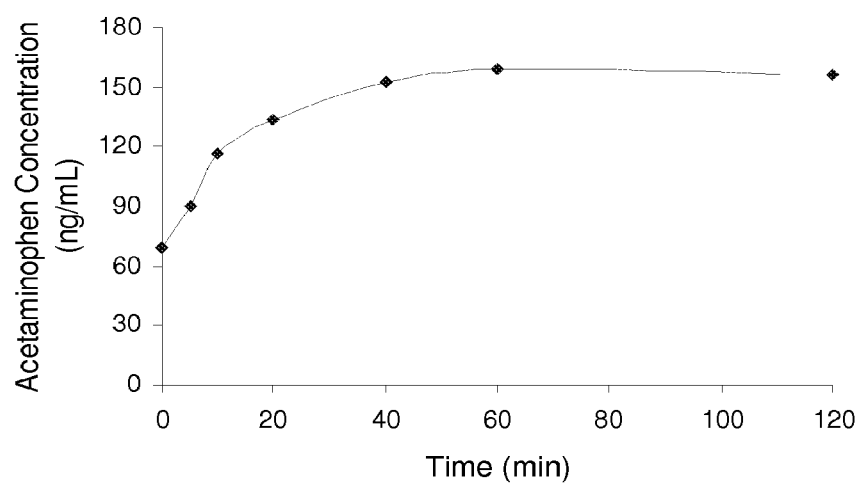
FIG. 2 shows the formation of acetaminophen from 0.3 µg/mL prodrug in human plasma.

A known amount of acetaminophen prodrug was incubated with human plasma samples maintained at physiological temperature. Small aliquots were drawn at predefined time points (0, 5, 10, 15, 20, 25, 30, 40, 60 and 120 minutes) and analyzed for acetaminophen content. The experiment was performed with two different concentrations of prodrug in pooled human plasma at 37° C. to determine kinetics of metabolic reaction and whether or not saturation of enzymatic system involved in conversion of prodrug to acetaminophen drug takes place. It was found that acetaminophen appeared by the time of first sample collection at nominal 0 minutes, and the concentration increased over the duration of 60 minutes, as shown in FIGS. 1 and 2.

Example 5: In Vivo Conversion of Acetaminophen Prodrug to Acetaminophen

Conversion of acetaminophen prodrug to acetaminophen through metabolism in the body was studied in rats. Similar to experimental design described above for in vitro studies, the acetaminophen prodrug was intravenously administered to the test animal and blood was drawn at predefined time points. The blood was analyzed for acetaminophen content or acetaminophen content alone, and the half-life of prodrug was determined.

Figure 3:
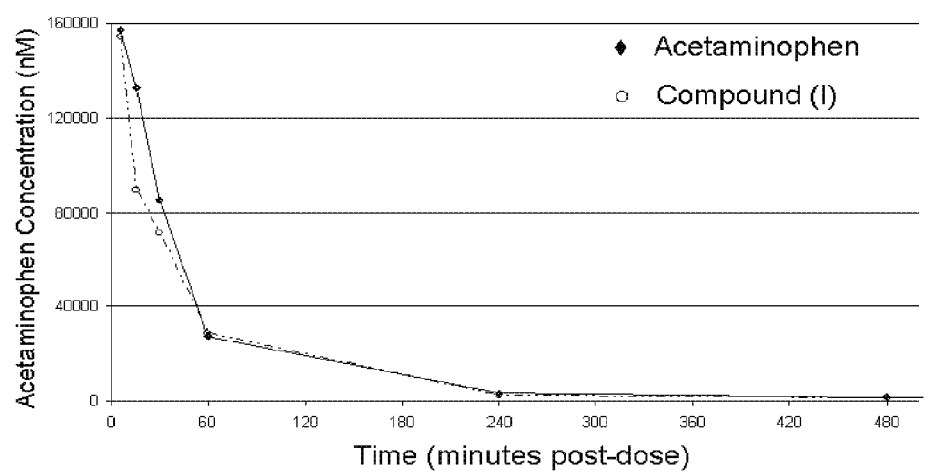
FIG. 3 shows the pharmacokinetic profile of acetaminophen in rats with time-dependent plasma concentration of the compound of formula (I) compared to the parent drug acetaminophen.

The pharmacokinetics of acetaminophen and the compound of formula I were evaluated after intravenous (IV) administration in order to determine resulting plasma acetaminophen concentrations. Acetaminophen and compound I were dosed on an equimolar basis to provide the same level of exposure (25 mg/kg) to acetaminophen and to obtain the profile of compound of formula I conversion in vivo to acetaminophen. The test animals were male and female Sprague Dawley (CD® IGS) rats (Charles River Laboratories), 7 to 8 weeks of age, weighing 220 to 270 grams. The rats were serially bled at 7 time points: 5, 15, 30 minutes and 1, 4, 8 and 24 hours post-dose. Whole blood samples (300 µL) were collected from the tail vein in lithium heparin microcontainers, processed to plasma by centrifugation and plasma was stored frozen at −70° C. until analyzed. Results of plasma analyses for acetaminophen content are shown in FIG. 3 and Table 2.

TABLE 2

Summary of calculated pharmacokinetic parameters of acetaminophen after intravenous administration of compound I to rats

| PK Parameter | Acetaminophen | | Prodrug (Acetaminophen) | |
|---|---|---|---|---|
| | Mean | % CV | Mean | % CV |
| Dose (mg/kg) | 25 | N.A. | 25* | N.A. |
| Half life (hr) | 2.65 | 43.7 | 2.12 | 48.3 |
| $T_{max}$ (hr) | 0.139 | 62.2 | 0.083 | 0.00** |
| $C_{max}$ (ng/mL) | 26467 | 22.8 | 30917 | 11.5 |
| $AUC_{0-8}$ (hr · ng/mL) | 24300 | 33.6 | 21233 | 20.7 |
| Clearance (mL/min/kg) | 19.5 | 40.5 | 20.3 | 19.2 |
| $V_{ss}$ (L/kg) | 1.48 | 25.0 | 1.52 | 23.1 |

*molar equivalent of 25 mg/kg acetaminophen
**all values the same

The invention claimed is:

1. A compound of formula (I):

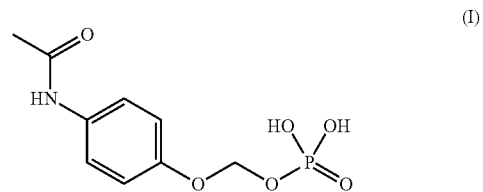

or a pharmaceutically acceptable salt thereof or solvate of the foregoing.

* * * * *